United States Patent
Yamada et al.

(10) Patent No.: US 10,939,851 B2
(45) Date of Patent: Mar. 9, 2021

(54) BRAIN-FUNCTIONAL NEAR INFRARED SPECTROSCOPY DEVICE AND MEASUREMENT METHOD

(71) Applicant: NATIONAL INSTITUTE OF ADVANCED INDUSTRIAL SCIENCE AND TECHNOLOGY, Tokyo (JP)

(72) Inventors: Toru Yamada, Tsukuba (JP); Shinji Umeyama, Tsukuba (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 526 days.

(21) Appl. No.: 15/551,102

(22) PCT Filed: Feb. 10, 2016

(86) PCT No.: PCT/JP2016/053955
§ 371 (c)(1),
(2) Date: Aug. 15, 2017

(87) PCT Pub. No.: WO2016/132989
PCT Pub. Date: Aug. 25, 2016

(65) Prior Publication Data
US 2018/0028098 A1    Feb. 1, 2018

(30) Foreign Application Priority Data
Feb. 16, 2015  (JP) .............................. JP2015-027690

(51) Int. Cl.
*A61B 5/1455*  (2006.01)
*A61B 10/00*  (2006.01)
*A61B 5/00*  (2006.01)

(52) U.S. Cl.
CPC .......... *A61B 5/1455* (2013.01); *A61B 5/4064* (2013.01); *A61B 5/6814* (2013.01); *A61B 5/7203* (2013.01); *A61B 10/00* (2013.01)

(58) Field of Classification Search
CPC ..... A61B 5/1455; A61B 10/00; A61B 5/4064; A61B 5/6814; A61B 5/7203; A61B 5/0075; A61B 5/7235; A61B 5/7275
See application file for complete search history.

(56) References Cited

U.S. PATENT DOCUMENTS 8,954,133 B1* 2/2015 Hanlon ................ A61B 5/0075
600/475
9,554,738 B1* 1/2017 Gulati .................. A61B 5/1455
(Continued)

FOREIGN PATENT DOCUMENTS

| CN | 104224165 A | 12/2014 |
|----|----|----|
| JP | 2009268707 A | 11/2009 |

(Continued)

OTHER PUBLICATIONS

Shinji Umeyama et al., "Detection of an Unstable and/or a Weak Probe Contact in a Multichannel Functional Near-Infrared Spectroscopy Measurement", Journal of Biomedical Optics 18(4), 047003 (Apr. 2013).
(Continued)

*Primary Examiner* — Hien N Nguyen
(74) *Attorney, Agent, or Firm* — Cantor Colburn LLP

(57) ABSTRACT

Provided is a multi-channel brain-functional near infrared spectroscopy device capable of easily levelling detector noise. The following control is performed: setting transmittances of all of optical attenuators to 1, setting intensities of all of light sources to a maximum light intensity within a safe irradiation range; determining the effective illumination intensity of each light source probe i as well as a minimum effective illumination intensity and a maximum effective illumination intensity thereof; changing the transmittance $a_i$ of each optical attenuator i on the light source probe side to [the minimum effective illumination intensity/effective illumination intensity of each light source probe i], thereby (Continued)

levelling the effective illumination intensity; and increasing the intensities of all of the light sources by W=[the maximum effective illumination intensity/the minimum effective incident efficiency] times, and determining the effective detection rate of each detector probe j as well as the minimum effective detection rate thereof; and performing control so as to level the effective detection rate by changing the transmittance $a_j$ of each optical attenuator j on the detector probe side to [the minimum effective detection rate/effective detection rate of each detector probe j], thereby equalizing detector noise among all the channels k.

2 Claims, 1 Drawing Sheet

(56) References Cited

U.S. PATENT DOCUMENTS

| | | |
|---|---|---|
| 2006/0006343 A1 | 1/2006 | Tanaka et al. |
| 2013/0102907 A1 | 4/2013 | Funane et al. |

FOREIGN PATENT DOCUMENTS

| | | |
|---|---|---|
| JP | 201483069 A | 12/2014 |
| JP | 2014083069 A | 12/2014 |

OTHER PUBLICATIONS

Toru Yamada et al., "Use of the Wavelength Differential Method of Eliminate Baseline Drift in the Assessment of Cerebral Function Using NIRS", Sep. 8, 2005, pp. 530-537, 43 (4).

* cited by examiner

○ : Light Irradiation Probes
● : Light Detection Probes a						b

BRAIN-FUNCTIONAL NEAR INFRARED SPECTROSCOPY DEVICE AND MEASUREMENT METHOD

TECHNICAL FIELD

The present invention relates to a brain-functional near infrared spectroscopy device and measurement method.

BACKGROUND ART

A brain-functional near infrared spectroscopy method (i.e., functional near-infrared spectroscopy; hereinafter also abbreviated as "fNIRS") is a method of measuring the dynamics of oxyhemoglobin and deoxyhemoglobin that change along with the activities of cerebral nerves, utilizing a property that hemoglobin in the blood has different spectral absorption properties in the near-infrared region when carrying oxygen (oxyhemoglobin) and when not carrying oxygen (deoxyhemoglobin), and has been regarded as one of the important methods for non-invasively detecting brain function activities. Usually, a light source and a detector are arranged at a distance of 30 mm from each other above the scalp. Near-infrared light with a plurality of wavelengths is caused to pass through surface layer tissue from the light source and reach brain tissue, and the change in hemoglobin in each state is measured depending on the light intensity that has returned to the detector on the surface of the head as well as the spectral absorption properties of hemoglobin. Such a light source and a detector are called probes, and a pair of a light source and a detector that are arranged and used for measurement in this manner is called a channel.

In such measurement, contact between each probe and living tissue is very important. A probe usually has a window with a diameter of several millimeters, whereas the spacing between hairs on the head of a human, or even an adult are about 1 millimeter. Therefore, it is practically difficult to remove all of hairs immediately below the window and allow the probe to contact the scalp. Accordingly, light attenuation always occurs between the scalp and the probe, and the amount of such light attenuation differs depending on the volume of hairs immediately below the probe and the degree of contact between the probe and the scalp. Therefore, when multi-channel measurement in which a number of such probes are arranged in parallel is performed, the light intensity detected greatly differs from channel to channel.

In response to the foregoing circumstances, commercially available multi-channel fNIRS devices first perform tentative measurement to conduct a calibration process of amplifying a detector signal to an appropriate level for a channel in which the light intensity is insufficient. This is in order to effectively use the resolution of an A/D converter during measurement. The original signal contains the light intensity and noise. However, as the degree of amplifying the original signal differs from channel to channel, a signal obtained through such a calibration process will have noise components (noise dispersion) that differ for each channel. For example, a device that uses photomultiplier tubes as detectors has noise derived from dark current that differs from channel to channel by as large as about 20 times when a voltage between 700 V and 1000 V, which is in the range of the normal calibration process, is applied. Therefore, prior to execution of the actual measurement, an operation of carefully removing hairs immediately below probes of a channel in which the light intensity is insufficient and noise is large is repeated, and compromise is reached at a certain stage to start collecting data. This operation is a bottle neck that takes much labor and time in the multi-channel fNIRS measurement. In addition, the measured data has large variations in quality depending on the degree of proficiency of an experimenter who attaches the probes as well as the volume, color, and the like of hairs of a test subject or a measurement position (see Patent Literature 1 and Non Patent Literature 1).

Further, using such a signal intensity calibration method becomes a big obstacle in performing statistical analysis of signals as indicated below. Multi-channel fNIRS devices often use, as a typical form of operation, a method of measuring changes in brain-functional activities for multiple channels in an area of a certain degree of size, and inspecting at which portion of the measured region the activity has been prominent. Meanwhile, most of the orthodox statistical analysis methods are designed based on a premise that sample groups should have equal dispersions. Therefore, it has been impossible to apply the strict statistical analysis to the fNIRS measured data having noise dispersion in a signal that greatly differs from channel to channel, and consequently, a statistical formulation for quantitative comparison among multi-channel data has not been developed yet.

CITATION LIST

Patent Literature

Patent Literature 1: JP2014-83069 A

Non Patent Literature

Non Patent Literature 1: S. Umeyama and T. Yamada, "Detection of an unstable and/or a weak probe contact in a multichannel functional near-infrared spectroscopy measurement", Journal of Biomedical Optics, 18(4), 047003, 2013.

SUMMARY OF INVENTION

Technical Problem

The present invention solves such difficulties in the multi-channel fNIRS measurement, that is, the problems of the complex operation of attaching probes and the difference in the noise levels of data among channels. Specifically, a systematic method is proposed that minimizes noise levels and dispersion among all measurement channels and by increasing the incident light intensity within the safe range for living tissues.

Solution to Problem

In order to solve the aforementioned problems, the present invention provides a brain-functional near infrared spectroscopy device, including n light source probes i (where $1 \leq i \leq n$) and m detector probes j (where $n+1 \leq j \leq n+m$) each arranged on a surface of a head; an optical attenuator i configured to guide light at a wavelength $\lambda$ from each light source to each light source probe i, at a transmittance $a_i$; an optical attenuator j configured to transmit light with the wavelength $\lambda$ detected with each detector probe j to a measurement data unit, at a transmittance $a_j$; and control means for processing detected data received by the measurement data unit to detect a brain function activity from a change in absorbance of measured light on the basis of spectral absorption properties of oxyhemoglobin and deoxyhemoglobin in N channels k (where $1 \leq k \leq N$) each including one of the light source probes i and one of the detector probes j. The control performs the following in advance: (1) setting transmittances of all of the optical attenuators to 1, setting intensities of all of the light sources to a maximum light intensity within a safe irradiation range, and determining an effective illumination intensity of each light source probe i as well as a minimum effective illumination intensity and a maximum effective illumination intensity thereof, and changing the transmittance $a_i$ of each optical attenuator i on the light source probe side to a value obtained by dividing the minimum effective illumination intensity by the effective illumination intensity of each light source probe i, thereby levelling the effective illumination intensity, and (2) increasing the intensities of all of the light sources by W times (where W=the maximum effective illumination intensity/the minimum effective illumination intensity), and determining the effective detection rate of each detector probe j as well as the minimum effective detection rate thereof, and then performing control so as to level the effective detection rate by changing the transmittance $a_j$ of each optical attenuator j on the detector probe side to a value obtained by dividing the minimum effective detection rate by the effective detection rate of each detector probe j, thereby equalizing dispersion of detector noise of oxyhemoglobin and dispersion of detector noise of deoxyhemoglobin among all the channels k.

In addition, the present invention provides a brain-functional near infrared spectroscopy method, including arranging n light source probes i (where $1 \leq i \leq n$) and m detector probes j (where $n+1 \leq j \leq n+m$) on a surface of a head; guiding, via an optical attenuator i, light with a wavelength λ from each light source to each light source probe i, at a transmittance $a_i$; transmitting, via an optical attenuator j, light with the wavelength λ detected with each detector probe j to a measurement data unit, at a transmittance $a_j$; processing detected data received by the measurement data unit to detect a brain function activity from a change in absorbance of measured light on the basis of spectral absorption properties of oxyhemoglobin and deoxyhemoglobin in N channels k (where $1 \leq k \leq N$) each including one of the light source probes i and one of the detector probes j, the method further including a step of attaching all of the light source probes i and all of the detector probes j to the surface of a head, and setting transmittances of all of the optical attenuators to 1, setting intensities of all of the light sources to a maximum light intensity within a safe irradiation range, and determining an effective illumination intensity of each light source probe i as well as a minimum effective illumination intensity and a maximum effective illumination intensity thereof; a step of changing the transmittance $a_i$ of each optical attenuator i on the light source probe side to a value obtained by dividing the minimum effective illumination intensity by the effective illumination intensity of each light source probe i, thereby levelling the effective illumination intensity; a step of increasing the intensities of all of the light sources by W times (where W=the maximum effective illumination intensity/the minimum effective illumination intensity), and determining the effective detection rate of each detector probe j as well as the minimum effective detection rate thereof; and a step of levelling the effective detection rate by changing the transmittance $a_j$ of each optical attenuator j on the detector probe side to a value obtained by dividing the minimum effective detection rate by the effective detection rate of each detector probe j, thereby equalizing in advance dispersion of detector noise of oxyhemoglobin and dispersion of detector noise of deoxyhemoglobin among all the channels k.

Advantageous Effects of Invention

The conventional brain-functional near infrared spectroscopy device is further provided with optical attenuators i at positions between light sources and light source probes i, and is also provided with optical attenuators j at positions between detector probes j and a measurement data unit. The transmittance $a_i$ of each optical attenuator i on the light source probe side is changed in advance by a control device so as to level the effective amounts of incident light. Next, the transmittance $a_j$ of each optical attenuator j on the detector probe side is changed so as to level the effective detection rate, whereby dispersion of detector noise of oxyhemoglobin and dispersion of detector noise of deoxyhemoglobin can be equalized among all channels k.

DESCRIPTION OF EMBODIMENTS

Figure 1:
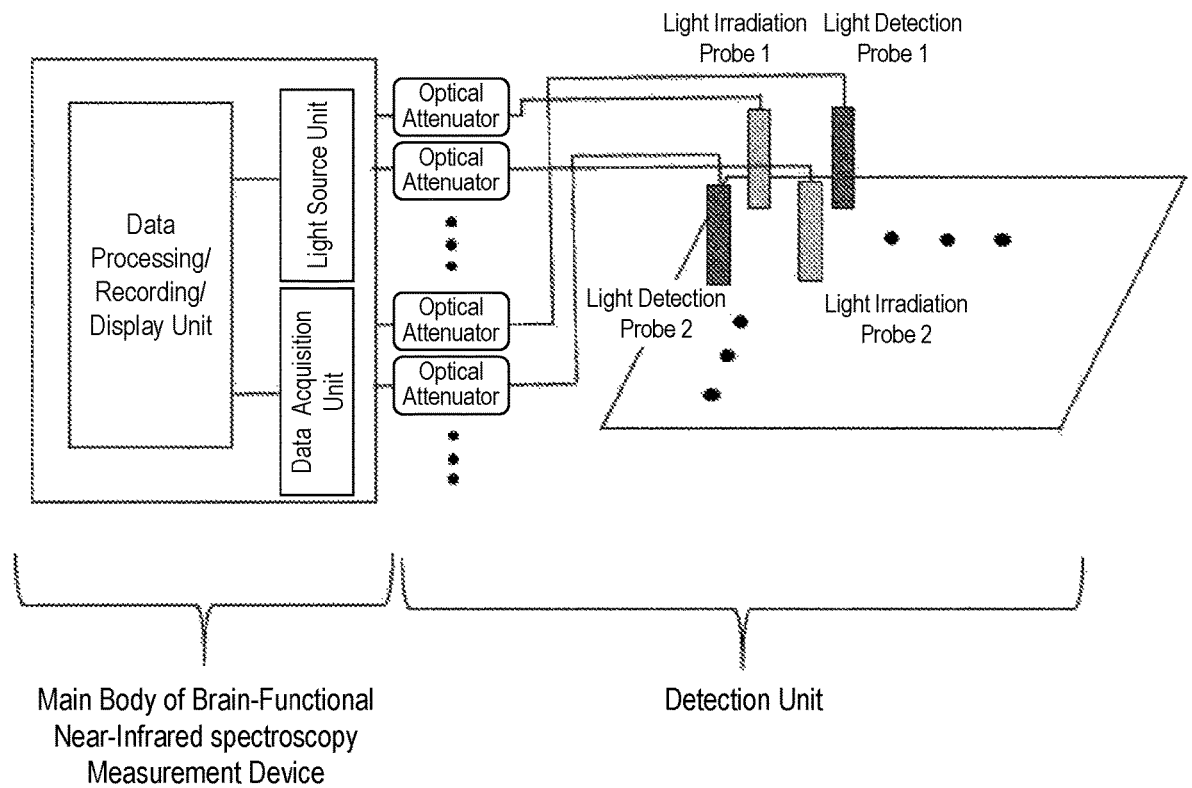
FIG. 1 is a diagram illustrating an embodiment of a brain-functional near infrared spectroscopy device of the present invention.

The inventors considered that the difficulty in performing statistical comparison between channels in multi-channel fNIRS measurement essentially results from the fact that apparent noise dispersion in a signal has varied due to a signal amplification factor changed in accordance with the detected light intensity, and thus attempted to solve the problem by individually introducing an optical attenuator for each probe and increasing or reducing the light intensity to control the noise dispersion. However, in multi-channel measurement in which both a plurality of light source probes and a plurality of detector probes are used in a complex manner, adjustment of a single optical attenuator will influence the noise dispersion of a plurality of associated channels. Therefore, the inventors have formulated a systematic method for adjusting a plurality of optical attenuators to thereby provide a measurement device and a measurement method that realize equalized and minimized noise dispersion among channels regardless of a channel arrangement within the range that the maximum illumination intensity is within the safety criterion for living tissues.

First of all, a loss of light that occurs in the whole process in which light with each wavelength emitted from the light source unit is collected by a detector in the detection unit during measurement is considered. Provided that the number of light source probes is n, the number of detector probes is m, a pair of a light source probe and a detector probe form a single channel, and the total number of channels in the device is N, it is known that a change in the absorbance of detected light with a wavelength of λ in a channel k (where $1 \leq k \leq N$), which is formed by a light source probe i (where $1 \leq i \leq n$) and a detector probe j (where $n+1 \leq j \leq n+m$), can be represented by the following Equation (1) (see Equation (13) of Patent Literature 1 above of the inventors or Equation (12) of Non Patent Literature 1).

[Math. 1]

$$\Delta A_{k,\lambda}(t) = -\log \frac{R_{k,\lambda}(t)}{R_{k,\lambda}(0)} - \log \frac{\tilde{r}_{i,\lambda}(t)\tilde{r}_{j,\lambda}(t)}{\tilde{r}_{i,\lambda}(0)\tilde{r}_{j,\lambda}(0)} - \frac{n_{j,\lambda}(t)}{I_{k,\lambda}a_i\tilde{r}_{i,\lambda}(t)r_{i,0,\lambda}R_{k,\lambda}(t)\tilde{r}_{j,\lambda}(t)r_{j,0,\lambda}a_j} \quad (1)$$

Herein, $\Delta A_{k,\lambda}(t)$ represents an absorbance change in the channel k; $R_{k,\lambda}(t)$ represents the tissue transmittance in the channel k; $I_{k,\lambda}$ represents the incident light intensity from the light source probe i; and $n_{j,\lambda}(t)$ represents noise generated in the detector during measurement with the detector probe j. In addition, temporal changes in the transmittance in accordance with light attenuation between the light source probe/detector probe and the scalp are represented by $\tilde{r}_{i,\lambda}(t)r_{i,0,\lambda}$, $\tilde{r}_{j,\lambda}(t)r_{j,0,\lambda}$, and it has been found that the temporal changes in the transmittance fluctuate as fluctuation patterns $\tilde{r}_{i,\lambda}(t)$, $\tilde{r}_{j,\lambda}(t)$ around given averages $r_{i,0,\lambda}$, $r_{j,0,\lambda}$ (see Patent Literature 1 and Non Patent Literature 1). Further, the transmittance at the wavelength $\lambda$ of each optical attenuator i connected to each light source probe is represented by $a_i$ (where $1 \leq i \leq n$, $0 \leq a_i \leq 1$), and the transmittance at the wavelength $\lambda$ of each optical attenuator j connected to each detector probe is represented by $a_j$ (where $n+1 \leq j \leq n+m$, $0 \leq a_j \leq 1$).

The first term of the right-hand side of Equation (1) above indicates an absorbance change with a hemoglobin change in the tissue, and the second term indicates a base line fluctuation generated due to a body motion and the like. Further, the third term indicates noise resulting from measurement noise from the photodetector. In this specification, such noise is referred to as detector noise. Now, consider that a signal is filtered through a high-pass filter to observe detector noise. At this time, fluctuations of the transmittance between the probes and the scalp $\tilde{r}_{i,\lambda}(t)r_{i,0,\lambda}$, $\tilde{r}_{j,\lambda}(t)r_{j,0,\lambda}$ and fluctuations of the tissue transmittance $R_{k,\lambda}(t)$ are filtered because they are slack, and they become constant values as $r_{i,0,\lambda}$, $r_{j,0,\lambda}$, R. At this time, the level $h_{k,\lambda}(t)$ of detector noise in the channel k can be represented as follows.

[Math. 2]

$$h_{k,\lambda}(t) = \frac{n_{j,\lambda}(t)}{I_{k,\lambda} a_i r_{i,0,\lambda} R r_{j,0,\lambda} a_j} \qquad (2)$$

Herein, provided that the molar absorption coefficient matrix of oxyhemoglobin and deoxyhemoglobin at two observed wavelengths is represented $$E^{-1} = \begin{pmatrix} u_{11} & u_{12} \\ u_{21} & u_{22} \end{pmatrix},$$

by E and the inverse matrix thereof is represented by noise components $h_{oxy,k}(t)$ derived from detector noise included in the observed temporal changes of oxyhemoglobin are represented by the following Equation (3).

[Math. 3]

$$h_{oxy,k}(t) = \begin{pmatrix} u_{11} & u_{12} \end{pmatrix} \begin{pmatrix} h_{k,\lambda_1}(t) \\ h_{k,\lambda_1}(t) \end{pmatrix} = \qquad (3)$$

$$\frac{u_{11} n_{j,\lambda_1}(t)}{I_{k,\lambda_1} a_i r_{i,0,\lambda_1} R r_{j,0,\lambda_1} a_j} + \frac{u_{12} n_{j,\lambda_2}(t)}{I_{k,\lambda_2} a_i r_{i,0,\lambda_2} R r_{j,0,\lambda_2} a_j}$$

Since noise generated in all detectors is estimated to be white noise, and such a property is regarded as common to all of the individual detector elements (j) as well as a plurality of wavelengths ($\lambda$) for a single detector element, all of $n_{j,\lambda_1}(t)$ and $n_{j,\lambda_2}(t)$ are independent and homoscedastic. Provided that the standard deviation thereof is $\sigma_n$, dispersion of the detector noise $h_{oxy,k}(t)$ should be observed as seen in the following Equation (4).

[Math. 4]

$$\sigma_{oxy,k}^2 = \left( \frac{u_{11}^2}{I_{k,\lambda_1}^2 a_i^2 r_{i,0,\lambda_1}^2 R^2 r_{j,0,\lambda_1}^2 a_j^2} + \frac{u_{12}^2}{I_{k,\lambda_2}^2 a_i^2 r_{i,0,\lambda_2}^2 R^2 r_{j,0,\lambda_2}^2 a_j^2} \right) \sigma_n^2 = \qquad (4)$$

$$\left( \frac{u_{11}^2}{J_{k,\lambda_1}^2} + \frac{u_{12}^2}{J_{k,\lambda_2}^2} \right) \sigma_n^2$$

Similarly, noise dispersion of deoxyhemoglobin is represented by the following Equation (5).

[Math. 5]

$$\sigma_{deoxy,k}^2 = \left( \frac{u_{21}^2}{I_{k,\lambda_1}^2 a_i^2 r_{i,0,\lambda_1}^2 R^2 r_{j,0,\lambda_1}^2 a_j^2} + \frac{u_{22}^2}{I_{k,\lambda_2}^2 a_i^2 r_{i,0,\lambda_2}^2 R^2 r_{j,0,\lambda_2}^2 a_j^2} \right) \sigma_n^2 = \qquad (5)$$

$$\left( \frac{u_{21}^2}{J_{k,\lambda_1}^2} + \frac{u_{22}^2}{J_{k,\lambda_2}^2} \right) \sigma_n^2$$

Herein, $J_{k,\lambda}$ indicates the observed light intensity with the wavelength $\lambda$ in the channel k, and is represented by the following Equation (6).

[Math. 6]

$$J_{k,\lambda} = I_{k,\lambda} a_i r_{i,0,\lambda} R r_{j,0,\lambda} a_j \qquad (6)$$

Equalizing the dispersion of the observed detector noise $\sigma_{2oxy,k}$ or $\sigma_{2doxy,k}$ among the channels shall be hereafter referred to as "leveling." An object of the present invention is to realize this.

Now, if the ratio $\beta_k$ between the observed light intensity with two wavelengths is determined as the following Equation (7),

[Math. 7]

$$\beta_k = \frac{J_{k,\lambda_2}}{J_{k,\lambda_1}} = \frac{I_{k,\lambda_2} r_{i,0,\lambda_2} r_{j,0,\lambda_2}}{I_{k,\lambda_1} r_{i,0,\lambda_1} r_{j,0,\lambda_1}} \qquad (7)$$

Equations (4) and (5) above can be represented by the following Equations (8) and (9), respectively.

[Math. 8]

$$\sigma_{oxy,k}^2 = \frac{\sigma_n^2 (\beta_k^2 u_{11}^2 + u_{12}^2)}{J_{k,\lambda_2}^2} = \frac{\sigma_n^2 (u_{11}^2 + u_{12}^2 / \beta_k^2)}{J_{k,\lambda_1}^2} \qquad (8)$$

[Math. 9]

$$\sigma_{deoxy,k}^2 = \frac{\sigma_n^2 (\beta_k^2 u_{21}^2 + u_{22}^2)}{J_{k,\lambda_2}^2} = \frac{\sigma_n^2 (u_{21}^2 + u_{22}^2 / \beta_k^2)}{J_{k,\lambda_1}^2} \qquad (9)$$

$I_{i,\lambda_2}/I_{i,\lambda_1}$ that form $\beta_k$ in Equation (7) above is a constant determined in accordance with the settings of the light source intensity for each wavelength. In addition, $r_{i,0,\lambda_2}/r_{i,0,\lambda_1}$ and $r_{j,0,\lambda_2}/r_{j,0,\lambda_1}$ indicate the wavelength dependence of the light transmittance in the air between the scalp and each probe, and can be regarded as a constant that is independent of the probe position. Therefore, $\beta_k$ is a constant that is independent of the channel position. Further, since $u_{x,y}$ is also a constant that is determined by the wavelength used and the absorption properties of hemoglobin, the denominators of Equations (8) and (9) are all constants. In order to level noise, it is found to be acceptable as long as the transmittances $a_i, a_j$ of the optical attenuators are adjusted so that the observed light intensity $J_{k,\lambda 1}$ or $J_{k,\lambda 2}$ becomes equal among the channels. In the actual adjusting operation, the observed light intensity is influenced by fluctuations of the transmittance between each probe and the scalp or of tissue. However, measuring the light intensity that has passed through a low-pass filter with an appropriate frequency band can easily eliminate such influence. Through such adjustment, noise of oxyhemoglobin and deoxyhemoglobin can be levelled concurrently.

However, in multi-channel brain-functional near infrared spectroscopy, a single light source probe is usually used for measurement of a plurality of adjacent channels. This is also the same for a detector probe. Therefore, it is quite often the case that when, in order to change the observed light intensity in a given channel, the associated optical attenuator is adjusted, the observed light intensity in an adjacent channel can also change. In this manner, it is not as easy as it looks to perform an operation of equalizing the observed light intensity in all channels under the conditions that the plurality of probes operate in a complex manner.

Herein, in the present invention, the light source side and the detector side are separately considered, and the aforementioned operation is realized through (1) an operation of equalizing the light intensity that actually becomes incident on tissue of the head (hereinafter referred to as "effective illumination intensity") among all the light source probes and (2) an operation of equalizing the rate of actually detecting light emerging from the tissue of the head (hereinafter referred to as "effective detection rate") among all the detector probes. To that end, specific procedures for formulating a method of estimating the effective illumination intensity and the effective detection rate for a given channel, and then leveling detector noise on the basis of real-time monitoring of the estimated amounts will be described next.

The observed light intensity is represented by a relational expression of the product of each variable as indicated by Equation (6) above. Taking the logarithm of Equation (6), the following Equation can be provided as a relational expression of the linear sum of each variable.

[Math. 10]

$$\log J_{k,\lambda} = \log(I_{i,\lambda}a_i r_{i,0,\lambda_j}C_1) + \log(r_{j,0,\lambda_j}a_j C_2) \quad (10)$$

It should be noted that:

[Math. 11]

$$C_1 C_2 = R \quad (11)$$

Herein, the first term $I_{i,\lambda}a_i r_{i,0,\lambda_j}$ of Equation (10) indicates the effective illumination intensity, and the second term $r_{j,0,\lambda_j}a_j$ indicates the effective detection rate.

Next, the relationship between a channel being measured and probes that form the channel is represented by a matrix called a probe arrangement matrix as in Patent Literature 1 of the inventors and Non Patent Literature 1. The probe arrangement matrix G is a matrix of N×(n+m), and when the light source probe i and the detector probe j form the channel k, the elements are defined as follows.

[Math. 12]

$$g_{kl} = \begin{cases} 1 & \text{if } l = i \text{ or } l = j \\ 0 & \text{otherwise} \end{cases} \quad (12)$$

Figure 2:
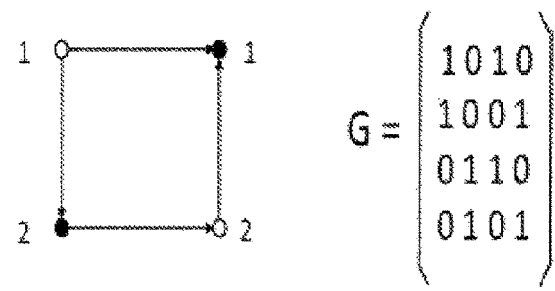
FIG. 2 is a diagram illustrating an exemplary arrangement of light irradiation probes (light source probes) and light detection probes (detector probes) in accordance with the present invention and a probe arrangement matrix thereof.

G differs depending on the channel/probe arrangement adopted in each fNIRS device. For example, when four channels are formed as in a of FIG. 2 using two light source probes and two detector probes, G becomes b as illustrated in FIG. 2. Whatever scale or channel/probe arrangement of patterns is adopted, only one G is always determined correspondingly, and also, only one $G^+$, which is a pseudo-inverse matrix of G, is determined correspondingly. With the probe arrangement matrix G, the relational expression of Equation (7) concerning a given channel can be represented as the following matrix arithmetic expression:

[Math. 13]

$$s_\lambda = G \rho_\lambda \quad (13)$$

Herein, $s_\lambda$ is a column vector having as elements log $J_{k,\lambda}$ (where $1 \le k \le N$), logarithms of the observed light intensity, and is provided through actual measurement. Meanwhile, $\rho_\lambda$ is a column vector represented by the following Equation (14) having as elements of a term log $(I_{i,\lambda}a_i r_{i,0,\lambda}C_1)$ (where $1 \le i \le n$) concerning the effective illumination intensity to be estimated and a term log $(r_{j,0,\lambda}a_j C_2)$ (where $n+1 \le j \le n+m$) concerning the effective detection rate.

[Math. 14]

$$\rho_\lambda = \begin{pmatrix} \log(I_{1,\lambda}a_1 r_{1,0,\lambda}C_1) \\ \vdots \\ \log(I_{n,\lambda}a_n r_{n,0,\lambda}C_1) \\ \log(r_{n+1,0,\lambda}a_{n+1}C_2) \\ \vdots \\ \log(r_{n+m,0,\lambda}a_{n+m}C_2) \end{pmatrix} \quad (14)$$

When Equation (13) is multiplied by $G^+$ from the left-hand side, the particular solution of $\rho_\lambda$ is determined as follows.

[Math. 15]

$$G^+ s_\lambda = \begin{pmatrix} b_{1,\lambda} \\ \vdots \\ b_{n,\lambda} \\ b_{n+1,\lambda} \\ \vdots \\ b_{n+m,\lambda} \end{pmatrix} \quad (15)$$

When Equations (14) and (15) above are compared, the following relation is obtained.

[Math. 16]

$$I_{i,\lambda}a_i r_{i,0,\lambda}C_1 = e^{b_{i,\lambda}} \quad (16)$$

[Math. 17]

$$r_{j,0,\lambda}a_j C_2 = e^{b_{j,\lambda}} \quad (17)$$

Therefore, the effective illumination intensity and the effective detection rate can be estimated as $e^{b_{i,\lambda}}/C_1$ (where $1 \leq i \leq n$) and $e^{b_{j,\lambda}}/C_2$ (where $n+1 \leq j \leq n+m$), respectively. Herein, the effective illumination intensity is $e^{b_{i,\lambda}}/C_1$ is independent of the adjustment of $a_j$, and the effective detection rate $e^{b_{j,\lambda}}/C_2$ is independent of the adjustment of $a_i$. Therefore, it is possible to avoid the difficulty of mutual interference of the adjustments via a probe network that would otherwise occur if the observed light intensity $J_{k,\lambda}$ is directly levelled. Although the equations that represent the effective illumination intensity and the effective detection rate include undetermined coefficients $C_1$ and $C_2$, respectively, the present invention can complete the leveling procedures without such coefficients determined as described below.

(To be strict, when Equations (16) and (17) are derived by converting Equations (14) and (15) into exponential forms, respectively, new scaling constants other than $C_1$ and $C_2$ are generated. Therefore, the uniqueness of the constants among the probes should be discussed. In conclusion, such constants can be estimated to be unique for all probes in a given probe network. Hereinafter, (i) to (iv) below will be discussed in detail.

(i) The general solution of simultaneous indeterminate equations can be represented by the sum of a particular solution and the solution of an associated equation $G_{\rho\lambda}=0$.

(ii) When $G^+ s_\lambda$ is considered using the pseudo-inverse matrix $G^+$, since $GG^+ s_\lambda = GG^+ G_{\rho\lambda} = G_{\rho\lambda} = s_\lambda$, is the particular solution of $s_\lambda = G_{\rho\lambda}$.

(iii) Next, the associated equation $G_{\rho\lambda}=0$ is considered. Provided that the number of light source probes is n and the number of detector probes is m, the following x is determined as the solution of the associated equation.

$$x=(x_1, x_2, \ldots, x_n, y_1, y_2, \ldots, y_m)^T$$

When reconstruction of the observed light intensity $J_{k,\lambda}$ in the channel k, which is formed by the light source probe i and the detector probe j, from a given solution is considered, $J_{k,\lambda}=I_{i,\lambda} a_i r_{i,0,\lambda} C_1 C_2 r_{j,0,\lambda} a_j$ should be established from Equations (6) and (11). In order to satisfy this, $x_i+y_j=0$ should be satisfied in the solution of the associated equation. That is, $x_i=-y_j=c$ (herein, c is a given constant).

By the way, there is also a similar request for another channel k' that shares the light source probe i in common. Therefore, provided that a detector probe associated with the channel k' is j', $x_i+y_{j'}=0$ should be established.

Therefore, $y_j=y_{j'}$ is established. Similarly, $x_i=x_{i'}$ is established between channels that share the detector probe j in common.

Therefore, in a probe network configured to include channels that share a light source probe and a detector probe in common, $x=(c, c, \ldots, c, -c, -c, \ldots, -c)^T$ is established for all of the light source probes i and the detector probes j.

(iv) Accordingly, the general solution of $s_\lambda = G_{\rho\lambda}$ can be expressed as $\rho_\lambda = G^+ s_\lambda + (c, c, \ldots, c, -c, -c, \ldots, -c)^T$ with c as a given constant. This ensures that the scale constants included in the effective illumination intensity and the effective detection rate that are estimated with the method of the present invention have unique values among the probes and thus that such values can be mutually compared among the probes.

Leveling of detector noise in the brain-functional near infrared spectroscopy device of the present invention will be described. In the measurement device, the maximum light intensity that can be emitted from the light source probes in accordance with the safety guideline of illumination for living tissues is assumed to be $I_{safe}$. At this time, it is obvious that even the $$\max_i e^{b_{i,\lambda}}$$

maximum value of the effective illumination intensity of the light source probes is less than or equal to $I_{safe}$. Setting the effective illumination $$\max_i e^{b_{i,\lambda}}$$

intensity of all of the light source probes to be equal to is the method of realizing a noise-levelled condition with the most favorable measurement S/N while maintaining the safety for living tissues. However, in a condition in which such levelling has been achieved, there may be cases where the light intensity emitted from some light source probe may exceed $I_{safe}$. Thus, if the probe is detached from the surface of the head or is moved to the scalp portion with a less volume of hairs in such an unadjusted condition, excessive light irradiation can occur. Therefore, it becomes further necessary to avoid such a circumstance for the sake of safety. The procedures for levelling and measuring detector noise in which the aforementioned circumstance is taken into consideration are described below.

1. Attach the probes to the head, and then set the transmittances of all of the optical attenuators in the device to 1 and set the intensities of all of the light sources to $I_{safe}$.
2. With the settings of 1. above, select one of the two wavelengths λ, and estimate $e^{b_{i,\lambda}}$, $e^{b_{j,\lambda}}$ of each probe by following Equations (16) and (17), that is, the effective illumination intensity and the effective detection rate $e^{b_{i,\lambda}}/C_1$, $e^{b_{j,\lambda}}/C_2$.
3. Set the transmittance $a_i$ of each optical attenuator on the light source probe side as in the following Equation (18):

[Math. 18]

$$a_i = \frac{\min_i(e^{b_{i,\lambda}})}{e^{b_{i,\lambda}}}, \text{ that is, } \frac{\min_i(e^{b_{i,\lambda}}/C_1)}{e^{b_{i,\lambda}}/C_1} \tag{18}$$

and level the effective illumination intensity $e^{b_{i,\lambda}}/C_1$.

4. Next, increase the intensities of all of the light sources by W times as determined by the following Equation (19).

[Math. 19]

$$W = \frac{\max_i(e^{b_{i,\lambda}})}{\min_i(e^{b_{i,\lambda}})}, \text{ that is, } \frac{\max_i(e^{b_{i,\lambda}}/C_1)}{\min_i(e^{b_{i,\lambda}}/C_1)} \tag{19}$$

5. Set the transmittance $a_j$ of each optical attenuator on the detector probe side as in the following Equation (20):

[Math. 20]

$$a_j = \frac{\min_j(e^{b_{j,\lambda}})}{e^{b_{j,\lambda}}}, \text{ that is, } \frac{\min_j(e^{b_{j,\lambda}}/C_2)}{e^{b_{j,\lambda}}/C_2} \tag{20}$$

and level the effective detection rate $e^{b_{j,\lambda}}/C_2$.

6. Levelling of detector noise of oxyhemoglobin and deoxyhemoglobin is achieved through the aforementioned settings. Data is measured with such settings maintained.
7. Concurrently with the termination of the measurement, the state in 1. is restored or the outputs of all of the light sources are interrupted. It should be noted that as represented by Equations (18) to (20) above, the procedures can be performed irrespective of the undetermined coefficient $C_1$ or $C_2$ in all of the processes 1. to 7. above.

INDUSTRIAL APPLICABILITY

Although levelling of detector noise of a brain-functional near infrared spectroscopy device has been described above, the present invention can be applied as long as a probe network configured to include channels that share a light source probe and a detector probe in common is used.

The invention claimed is:

1. A brain-functional near infrared spectroscopy device, comprising:
   n light source probes i (where $1 \leq i \leq n$) and m detector probes j (where $n+1 \leq j \leq n+m$) each adapted to arrange on a surface of a head;
   an optical attenuator i configured to guide light with a wavelength $\lambda$ from each light source to each light source probe i, at a transmittance $a_i$;
   an optical attenuator j configured to transmit light with the wavelength $\lambda$ detected with each detector probe j to a measurement data unit, at a transmittance $a_j$; and
   control means for processing detected data received by the measurement data unit to detect a brain function activity from a change in absorbance of measured light on a basis of spectral absorption properties of oxyhemoglobin and deoxyhemoglobin in N channels k (where $1 \leq k \leq N$) each including one of the light source probes i and one of the detector probes j,
   wherein:
   the control means performs the following in advance:
   (1) setting transmittances of all of the optical attenuators to 1, setting intensities of all of the light sources to a maximum light intensity within a safe irradiation range, and determining an effective illumination intensity of said each light source probe i as well as a minimum effective illumination intensity and a maximum effective illumination intensity thereof, and
   changing the transmittance $a_i$ of each optical attenuator i on the light source probe side to a value obtained by dividing the minimum effective illumination intensity by the effective illumination intensity of said each light source probe i, thereby levelling the effective illumination intensity, and
   (2) increasing the intensities of all of the light sources by W times (where W=the maximum effective illumination intensity/the minimum effective illumination intensity), and determining an effective detection rate of said each detector probe j as well as a minimum effective detection rate thereof, and
   performing control so as to level the effective detection rate by changing the transmittance $a_j$ of each optical attenuator j on the detector probe side to a value obtained by dividing the minimum effective detection rate by the effective detection rate of each detector probe j, thereby equalizing dispersion of detector noise of oxyhemoglobin and dispersion of detector noise of deoxyhemoglobin among all the channels k.

2. A brain-functional near infrared spectroscopy method, comprising:
   arranging n light source probes i (where $1 \leq i \leq n$) and m detector probes j (where $n+1 \leq j \leq n+m$) on a surface of a head;
   guiding, via an optical attenuator i, light with a wavelength $\lambda$ from each light source to each light source probe i, at a transmittance $a_i$;
   transmitting, via an optical attenuator j, light with the wavelength $\lambda$ detected with each detector probe j to a measurement data unit, at a transmittance $a_j$;
   processing detected data received by the measurement data unit to detect a brain function activity from a change in absorbance of measured light on a basis of spectral absorption properties of oxyhemoglobin and deoxyhemoglobin in N channels k (where $1 \leq k \leq N$) each including one of the light source probes i and one of the detector probes j, the method further comprising:
   a step of attaching all of the light source probes i and all of the detector probes j to the surface of a head, and setting transmittances of all of the optical attenuators to 1, setting intensities of all of the light sources to a maximum light intensity within a safe irradiation range, and determining an effective illumination intensity of said each light source probe i as well as a minimum effective illumination intensity and a maximum effective illumination intensity thereof;
   a step of changing the transmittance $a_i$ of each optical attenuator i on the light source probe side to a value obtained by dividing the minimum effective illumination intensity by the effective illumination intensity of said each light source probe i, thereby levelling the effective illumination intensity;
   a step of increasing the intensities of all of the light sources by W times (where W=the maximum effective illumination intensity/the minimum effective illumination intensity), and determining an effective detection rate of said each detector probe j as well as a minimum effective detection rate thereof; and
   a step of levelling the effective detection rate by changing the transmittance $a_j$ of each optical attenuator j on the detector probe side to a value obtained by dividing the minimum effective detection rate by the effective detection rate of each detector probe j, thereby equalizing in advance dispersion of detector noise of oxyhemoglobin and dispersion of detector noise of deoxyhemoglobin among all the channels k.

* * * * *